(12) United States Patent
Pettersson et al.

(10) Patent No.: US 9,115,158 B2
(45) Date of Patent: Aug. 25, 2015

(54) THIONATING AGENT

(71) Applicant: VIRONOVA THIONATION AB, Stockholm (SE)

(72) Inventors: Birgitta Pettersson, Hagersten (SE); Vedran Hasimbegovic, Solna (SE); Per H Svensson, Stockholm (SE); Jan Bergman, Spanga (SE)

(73) Assignee: VIRONOVA THIONATION AB, Stockholm (SE)

( * ) Notice: Subject to any disclaimer, the term of this patent is extended or adjusted under 35 U.S.C. 154(b) by 0 days.

(21) Appl. No.: 13/936,423

(22) Filed: Jul. 8, 2013

(65) Prior Publication Data
US 2013/0303767 A1    Nov. 14, 2013

Related U.S. Application Data

(62) Division of application No. 13/807,104, filed as application No. PCT/EP2012/051864 on Feb. 3, 2012.

(60) Provisional application No. 61/439,522, filed on Feb. 4, 2011.

(30) Foreign Application Priority Data

Feb. 4, 2011 (EP) ..................................... 11153421

(51) Int. Cl.
*C07B 45/00* (2006.01)
*C07F 9/58* (2006.01)
(Continued)

(52) U.S. Cl.
CPC . *C07F 9/58* (2013.01); *C07B 45/04* (2013.01); *C07C 325/02* (2013.01); *C07C 327/48* (2013.01); *C07D 207/24* (2013.01); *C07D 207/416* (2013.01); *C07D 209/08* (2013.01); *C07D 209/30* (2013.01); *C07D 209/34* (2013.01); *C07D 209/42* (2013.01); *C07D 209/88* (2013.01); *C07D 211/72* (2013.01); *C07D 211/84* (2013.01); *C07D 211/88* (2013.01); *C07D 213/63* (2013.01); *C07D 213/70* (2013.01); *C07D 213/83* (2013.01); *C07D 215/36* (2013.01); *C07D 219/04* (2013.01); *C07D 219/08* (2013.01); *C07D 223/06* (2013.01); *C07D 239/58* (2013.01); *C07D 239/70* (2013.01); *C07D 239/93* (2013.01); *C07D 241/08* (2013.01); *C07D 241/44* (2013.01); *C07D 243/14* (2013.01); *C07D 243/22* (2013.01); *C07D 245/04* (2013.01); *C07D 309/36* (2013.01); *C07D 311/84* (2013.01); *C07D 341/00* (2013.01); *C07D 471/04* (2013.01);
(Continued)

(58) Field of Classification Search
CPC ....................................................... C07B 45/00
See application file for complete search history.

(56) References Cited

PUBLICATIONS

Fluck and Binder (Chemische Reaktionen Dr Perthiophosphonsaureanhydride; vol. 354, No. 3-4; Oct. 1967; pp. 113-124).*

(Continued)

*Primary Examiner* — Valerie Rodriguez-Garcia
(74) *Attorney, Agent, or Firm* — Young & Thompson

(57) ABSTRACT

A process for transforming a group >C=O (I) in a compound into a group >C=S (II) or into a tautomeric form of group (II) in a reaction giving a thionated reaction product, by use of crystalline $P_2S_5 \cdot 2C_5H_5N$ as a thionating agent. A thionating agent which is crystalline $P_2S_5 \cdot 2C_5H_5N$.

1 Claim, 2 Drawing Sheets

(51) Int. Cl.
| | |
|---|---|
| C07B 45/04 | (2006.01) |
| C07C 325/02 | (2006.01) |
| C07C 327/48 | (2006.01) |
| C07D 207/24 | (2006.01) |
| C07D 209/30 | (2006.01) |
| C07D 211/72 | (2006.01) |
| C07D 211/84 | (2006.01) |
| C07D 213/63 | (2006.01) |
| C07D 239/93 | (2006.01) |
| C07D 213/83 | (2006.01) |
| C07D 309/36 | (2006.01) |
| C07D 215/36 | (2006.01) |
| C07D 311/84 | (2006.01) |
| C07D 219/04 | (2006.01) |
| C07D 219/08 | (2006.01) |
| C07D 223/06 | (2006.01) |
| C07D 341/00 | (2006.01) |
| C07D 239/58 | (2006.01) |
| C07D 241/08 | (2006.01) |
| C07D 241/44 | (2006.01) |
| C07D 243/22 | (2006.01) |
| C07D 245/04 | (2006.01) |
| C07D 471/04 | (2006.01) |
| C07D 473/36 | (2006.01) |
| C07D 487/04 | (2006.01) |
| C07D 207/416 | (2006.01) |
| C07D 209/08 | (2006.01) |
| C07D 209/34 | (2006.01) |
| C07D 209/42 | (2006.01) |
| C07D 209/88 | (2006.01) |
| C07D 213/70 | (2006.01) |
| C07D 211/88 | (2006.01) |
| C07D 239/70 | (2006.01) |
| C07D 243/14 | (2006.01) |

(52) U.S. Cl.
CPC ........... C07D 473/36 (2013.01); C07D 487/04 (2013.01); C07F 9/581 (2013.01); C07B 45/00 (2013.01)

(56) References Cited

PUBLICATIONS

Baumann et al., "Ueber Thioaldehyde", E. Ber., 1889, vol. 22, pp. 2600-2609.
Bonini et al., "Chemistry of Silyl Thioketones. Part 4. 2,4,6-Triaryl-2,4,6-tris(trimethylsilyl)- 1,3,5-trithianes from Silyl Thioketones: Crystal Structure of 2,4,6-Triphenyl- 2,4,6-tris(trimethylsilyl)-1,3,5-trithiane and Stereochemistry of Desilylation with Fluoride Ion", J. Chem. Soc. Perkin Trans., 1988, vol. 1, pp. 1499-1502.
Bottcher et al., "Uber die Einwirkung von Diphosphorpentasulfid auf aromatische Aldehyde und Ketone", Annalen der Chemie, 1951, vol. 574, pp. 218-226.
Brunel et al., "Carbon—Phosphorus Bond Formation by Reaction of Pyridine and ita Monoethyl Derivatives with Tetraphosphorus Desasulfide." J. Chem. Research (M), 1981, pp. 3437-3445.
Fluck et al., "Uber die Reaktion der Phosphorsulfide P4S3 P4S5 P4S7 und P4S10 mit Ammoniak und Aminen", 1968, vol. 359, pp. 102-112.
Hino et al., "2-Indolinethiones. Tautomerism and Oxidation to the Disulfides", Pharmaceutical Society of Japan, Chem. Phaim. Bull., 1974, vol. 22, No. 5, pp. 1053-1060.
Jesberger et al., "Applications of Lawesson's Reagent in Organic and Organometallic Syntheses", 2003, No. 13, pp. 1929-1958.
Ley et al., "A polymer-supported thionating reagent", J. Chem. Soc., Perkins Trans., 2001, vol. 1, pp. 358-361.
Meisel et al., "Uber Thiophosphorsaure-pyrididiumbetaine", Anorg. Allg. Chemie, 1967, vol. 360, pp. 277-283.
Ozturk et al., "Use of Lawesson's Reagent in Organic Syntheses", Chem. Rev., 2007, vol. 107, pp. 5210-5278.
Ozturk et al., "A Berzelius Reagent, Phosphorus Decasulfide (P4S10), in Organic Syntheses", Chem. Rev., 2010, vol. 110, pp. 3419-3478.
Scheibye et al., "Reactions of Ketones with 2,4-Bis(4-Methoxyphenyl)- 1,3,2,4-Dithiadiphosphetane 2,4-Disulfide", C. Tetrahedron, 1982, vol. 38, pp. 993-1001.
Sekido et al., "Structure of the β Form of 2,4,6-Triphenyl-1,3,5-trithiane, C21H18S3", Acta Cryst., 1985, C41, pp. 397-400.
Stanfield et al., "Studies on Thioaldehydes. I. The Monohalothiobenzaldehydes", J. Am. Chem. Soc., 1952, vol. 74, pp. 2878-2880.
Stoyanov et al., "Thione-thiol tautomerism and stability of 2- and 4-mercaptopyridines and 2-mercaptopyrimidines", Can. J. Chem., 1990, vol. 68, pp. 1482-1489.
Takikawa et al., "Reactions of 2,4,6-Triaryl-Dihydro-1,3,5-Dithiazines with Electrophilic", The Chemical Society of Japan, Chemistry Letters, 1983, pp. 1503-1506.
International Search Report dated Jun. 12, 2012, corresponding to PCT/EP2012/051864.
Binder H. E. Fluck, et al.; "Chemische Reaktionen Dr Perthiophosphonsaureanhydride"; vol. 354, No. 3-4; Oct. 1967; pp. 113-224.
M. Meisel, et al.; "Uber Thiophosphorsaure-Pyridiniumbetaine"; vol. 360, 1968, pp. 277-283.
Klingsberg, et al.; Thiation with Phosphorus Pentasulfide in Pyridine Solution; J. Am. Chem. Soc.; vol. 73, No. 10; Oct. 1951.

* cited by examiner

US 9,115,158 B2

THIONATING AGENT

CROSS REFERENCE TO RELATED APPLICATIONS

This application is a division of copending application Ser. No. 13/807,104 filed on Dec. 27, 2012; which is the 35 U.S.C. 371 national stage of International application PCT/EP2012/051864 filed on Feb. 3, 2012; which claims the benefit of U.S. provisional application Ser. No. 61/439,522 filed Feb. 4, 2011 and claims priority to EP application 11153421.0 filed on Feb. 4, 2011. The entire contents of each of the above-identified applications are hereby incorporated by reference.

FIELD OF THE INVENTION

The present invention relates to a thionation process. More specifically, the invention relates to a process for transforming an oxo group (>C=O) in a compound into a thio group (>C=S) or a tautomeric form of said thio group.

BACKGROUND OF THE INVENTION

In 1951, Klingsberg[1] et al described the use of $P_4S_{10}$ dissolved in pyridine as a thionating agent. Pyridine and $P_4S_{10}$ react readily to form a zwitter-ionic, non-smelling compound, the composition of which, $P_2S_5.2C_5H_5N$, was studied as early as 1967-1968 by German inorganic chemists[2,3] who obtained evidence for its structure by $^{31}P$ NMR data[4] as well as by comparison with related molecules.

In spite of the teachings of Klingsberg et al., the predominantly used agent in the reaction of thionation of compounds containing an oxo group has been the so-called Lawesson's reagent (IUPAC name: 2,4-bis(4-methoxyphenyl)-1,3,2,4-dithiadiphosphetane-2,4-dithione), herein below referred to as LR. LR was introduced in 1968 for transformations in organic chemistry and was used with a considerable number of reactants, such as amides and ketones, which were thionated in fair yields. However, LR as a thionating agent suffers from a number of drawbacks. For example, its thermal stability is mediocre; it has even been reported that LR starts to decompose above 110° C.[5,6]. Further, LR has a generally low solubility, which quite often has necessitated the use of hexamethylphosphoramide (HMPA) as a solvent. HMPA is suspected of being carcinogenic to humans and its use is prohibited in many countries. Additional drawbacks with LR are the strong, unpleasant smell of the compound in itself and the fact that during a reaction, there tends to be formation of foul-smelling side-products that are difficult to separate from the desired reaction products (column chromatography is often required).

It appears that there still remains a need for an improved process for the thionation of an oxo group-containing compound as well as an improved thionating agent for use in such process.

SUMMARY OF THE INVENTION

According to a first aspect there is provided a process for transforming a group >C=O (I) in a compound into a group >C=S (II) or a tautomeric form of group (II), in a reaction giving a thionated reaction product, by use of crystalline $P_2S_5.2C_5H_5N$ as a thionating agent.

According to a further aspect, a thionating agent is provided, which is crystalline $P_2S_5.2C_5H_5N$.

DETAILED DESCRIPTION OF THE INVENTION

Figure 1A:
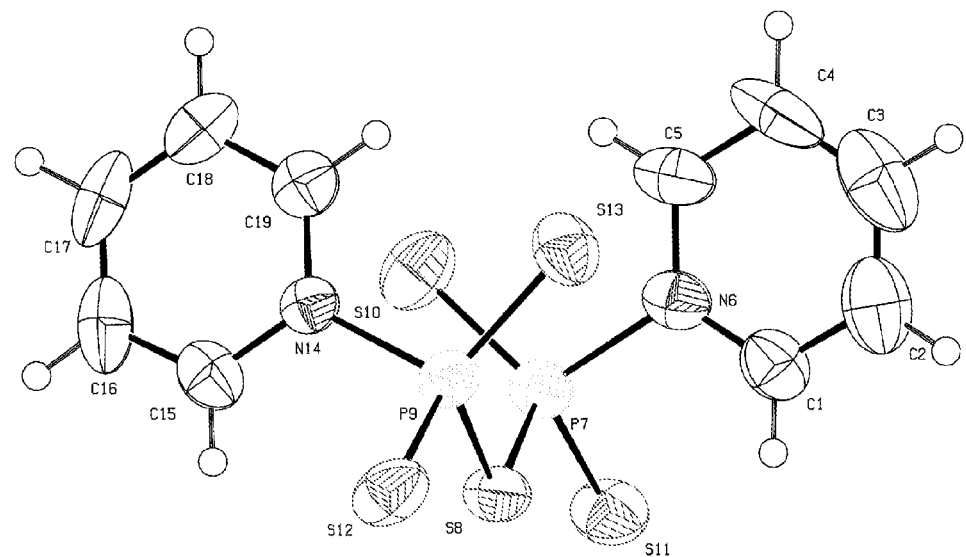
FIG. 1 shows (A) the molecular structure and (B) the crystal structure of $P_2S_5.2C_5H_5N$.
Figure 1B:
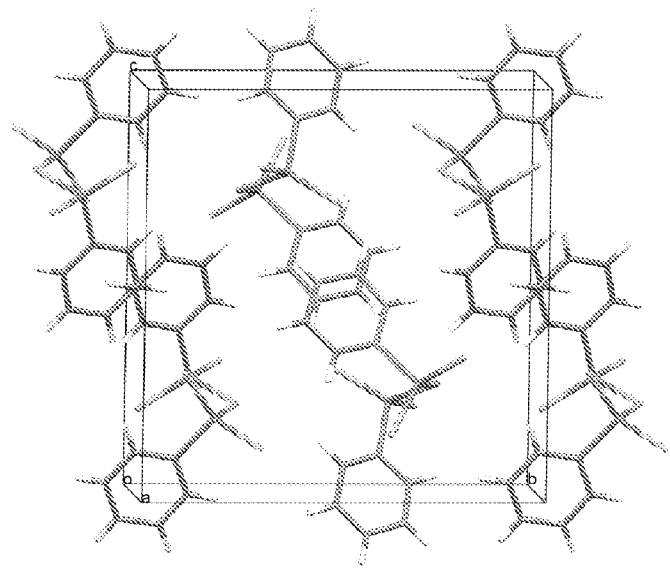

The present inventors have determined the crystal structure of $P_2S_5.2C_5H_5N$ by X-ray analysis, the details of which are given in the Experimental Section. An Ortep representation of the molecular structure of the compound is shown in FIG. 1. The molecules are linked together via several van der Waals interactions. The strongest van der Waals contact (C—H . . . S) links the molecules together into and infinite chain along the c-axis. The packing coefficient (percent filled van der Waals space in the unit-cell) is 67.7%, indicating an efficient molecular framework in the solid state. The molecular packing is facilitated by the aromatic π stacking. The distance between the planes of two adjacent aromatic moieties is approximately 3.5 Å.

As mentioned herein above, the present invention provides a thionating agent consisting of crystalline $P_2S_5.2C_5H_5N$. Very advantageously, this agent is storable for long period of times and moreover is free from impurities inherent in the conventional thionating agent because these impurities (from $P_4S_{10}$) are removed via the pyridine mother liquor.

The improved purity will result in cleaner thionation products and more facile work-up procedures. A particular advantage is the fact that the thionating agent can be transferred to solvents such as acetonitrile and dimethylsulfone.

Indeed, the zwitterionic crystalline compound has fair solubility in hot acetonitrile and a good solubility in hot pyridine. It also has a good solubility in cyclic sulfones or in lower alkyl sulfones, such as dimethylsulfone.

In one embodiment of the process of the invention, the thionating agent and the compound to be thionated are allowed to react in a liquid solvent medium for the compound and for the thionating agent. In other words, the thionating agent is used dissolved in a liquid solvent medium.

In one embodiment of the process of the invention, the thionating agent is used as a melt, mixed with the compound to be thionated. In this embodiment, the thionating agent is heated to its melting temperature (167-169° C.) and the compound to be thionated is mixed with the thionating agent before, after or during heating.

The solvent medium should be selected from aprotic solvents. In one embodiment, the liquid solvent medium is an organic solvent that is liquid at room temperature and that may be heated to a suitable reaction temperature, e.g. a temperature of 60-200° C., e.g. 60-100° C., such as acetonitrile that is a liquid at room temperature (melting point −42° C.) and has a boiling temperature of 82° C. In this case, the crystalline $P_2S_5.2C_5H_5N$ and the compound to be thionated are both dissolved in the organic solvent, which optionally is heated e.g. to reflux.

In one embodiment, the crystalline $P_2S_5.2C_5H_5N$ is admixed with the solvent medium, at a temperature below the melting point of the solvent medium and of the crystalline $P_2S_5.2C_5H_5N$ and the mixture is heated in order to obtain a liquid solution containing $P_2S_5.2C_5H_5N$ dissolved in the liquid solvent medium.

The compound to be thionated may be admixed with the other components of the reaction mixture at any point of the process, e.g. before or after melting and/or dissolution.

For example, the melting temperature of dimethylsulfone is 107-109° C. In case melted dimethylsulfone is used as a liquid solvent medium for the reaction, crystalline $P_2S_5.2C_5H_5N$ and solid dimethylsulfone may be mixed at e.g. room temperature and heated to a temperature of at least about 109° C., at which time a solution of $P_2S_5 \cdot 2C_5H_5N$ in liquid dimethylsulfone is obtained. In this reaction medium, the thionation of the oxo group containing compound may be performed.

An advantageous feature of $P_2S_5 \cdot 2C_5H_5N$ is its thermal stability, which allows for performing the thionating reaction at temperatures well over 100° C., e.g. at a temperature of 100-200° C., or 115-180° C., or at a temperature of 150-175° C., in particular at a temperature of 165-175° C., although also lower temperatures may be used, e.g. 60-100° C. In some embodiments, the reaction is performed at the boiling temperature of the liquid solvent medium.

It is at present not clear if it is $P_2S_5 \cdot 2C_5H_5N$ per se that, after dissolution in the liquid solvent medium, thionates the compound, or whether the reaction proceeds via dissociation to some other intermediary, reactive species. For the purpose of the present invention, however, the precise mechanism of the reaction is not essential, and by indication that the dissolved $P_2S_5 \cdot 2C_5H_5N$ is allowed to react with the dissolved compound it is intended to include a reaction proceeding by any possible intermediary leading to the desired thionated product.

In the presence of water or a protic solvent, such as a lower alcohol, e.g. methanol or ethanol, $P_2S_5 \cdot 2C_5H_5N$ quickly undergoes extensive degradation. For example, addition of water to a hot solution/suspension of $P_2S_5 \cdot 2C_5H_5N$ in acetonitrile will quickly result in a clear solution of a salt of pyridine and phosphorothioic acid, viz. pyridinium dihydrogenmonothiophosphate, of formula

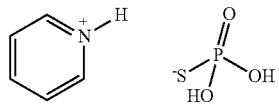

This salt is readily soluble in water and its ready formation and high solubility can be advantageously used during work-up of the thionated reaction product of the invention, e.g. thioamides. Thus, in a typical reaction of the invention, four equivalents of an amide are heated with 1.1 equivalents of crystalline $P_2S_5 \cdot 2C_5H_5N$ in dry acetonitrile and in connection with the work-up any remaining thionating agent is readily removed by addition of water.

$P_2S_5 \cdot 2C_5H_5N$ will also decompose when treated with alcohols; e.g. treatment of $P_2S_5 \cdot 2C_5H_5N$ with ethanol gives pyridinium O,O-diethyldithiophosphonate, of formula

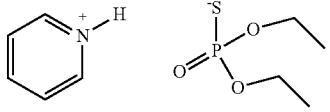

Thus, one advantage of the present invention is that the desired thionated product is easily separated from any remaining thionating agent $P_2S_5 \cdot 2C_5H_5N$ by treatment with a protic solvent, such as water or a lower alcohol, e.g. ethanol.

Therefore, in one embodiment of the invention, there is provided a process for transforming a group >C=O (I) in a compound into a group >C=S (II) or a tautomeric form of group (II) by bringing the compound into contact with $P_2S_5 \cdot 2C_5H_5N$ so as to obtain a thionated reaction product; comprising admixing crystalline $P_2S_5 \cdot 2C_5H_5N$ with said compound in a liquid solvent medium for the compound and for the crystalline $P_2S_5 \cdot 2C_5H_5N$, so as to obtain a liquid solution of the compound and $P_2S_5 \cdot 2C_5H_5N$, and allowing the $P_2S_5 \cdot 2C_5H_5N$ and compound to react with each other in the solution, followed by adding a protic solvent to the solution.

After addition of a protic solvent to the solution, the salt resulting from decomposition of any remaining $P_2S_5 \cdot 2C_5H_5N$ will be easily separated from the thionated compound, e.g. by extraction with an aqueous solution or with water. In some embodiments, addition of a protic solvent, such as water, will result in the precipitation of the thionated reaction product, which may then be separated from the aqueous phase, e.g. by a simple filtration. Further purification of the reaction product may optionally be performed, e.g. by recrystallization.

The group >C=O (I) to be transformed into a group >C=S (II) may be present e.g. in a ketone or an amide functional group and may be present in a compound comprising one or several functional groups, in which case a selective thionation may be achievable, as will be shown in the Examples herein below.

In one embodiment, the group (I) is present in an amide function, —C(O)—N<, e.g. in a compound

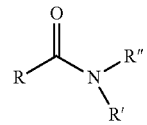

wherein R e.g. may be selected from C1-C12 hydrocarbyls, and R' and R" may be independently selected from H and C1-C12 hydrocarbyls, or wherein R and R' and/or R' and R" may be joined to each other to form, together with the amide carbon and/or nitrogen to which they are attached, a mono- or polycyclic ring, e.g. a mono- or polycyclic 5-20 membered ring optionally containing one or several additional heteroatoms, e.g. one or several heteroatoms selected from O, N and S, which ring may be saturated or unsaturated and aromatic or non-aromatic.

In one embodiment, the compound is a peptide, an oligopeptide or a polypeptide, e.g. a peptide comprising from 1 to 10 groups (I) in the backbone, or from 1 to 5 oxo groups (I).

In one embodiment, the group (I) is present in a ketone function, such as in a compound

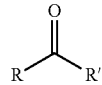

wherein R and R' e.g. may be independently selected from H and C1-C12 hydrocarbyls, or may be joined to each other to form, together with the ketone carbon, a mono- or polycyclic ring, e.g. a mono- or polycyclic 5-20 membered ring optionally containing one or several heteroatoms, e.g. one or several heteroatoms selected from O, N and S, which ring may be saturated or unsaturated and aromatic or non-aromatic.

The groups R, R' and R" may optionally and independently be substituted by one or more substituents, e.g. one or more further oxo groups or one or more other functional groups.

When the group (I) is present in a ketone function, there preferably should be at least one electron donating group present in the compound, resulting in an increased electron density of the group (I). Such electron donating group (EDG) e.g. may be a group having a lone electron pair, capable of raising the electron density of the keto group by delocalization of said electron pair through one or several double bonds situated between the EDG and the keto group. The electron density of the keto group also may be raised by inductive effects.

The product of the thionating reaction of the invention is a thionated compound comprising a group >C=S (II) or a tautomer thereof, e.g. a group >C=C(SH)—.

The crystalline $P_2S_5.2C_5H_5N$ preferably is admixed at a molar ratio to the group (I) to be transformed of 1 mole $P_2S_5.2C_5H_5N$ per 1-4 moles of group (I), e.g. 1 mole $P_2S_5.2C_5H_5N$ per 2-4 moles of group (I), in particular 1 mole $P_2S_5.2C_5H_5N$ per 3-4 moles of group (I). Therefore, in case the compound contains more than one group (I) to be transformed into a group (II), the molar ratio of $P_2S_5.2C_5H_5N$ to compound will be correspondingly higher. For example, in case the compound contains 2 groups (I) to be transformed into 2 groups (II), the crystalline $P_2S_5.2C_5H_5N$ preferably is admixed at a molar ratio with the compound to be thionated of 1 mole $P_2S_5.2C_5H_5N$ per 0.5-2 moles of the compound, e.g. 1 mole $P_2S_5.2C_5H_5N$ per 1-2 moles of the compound, or 1 mole $P_2S_5.2C_5H_5N$ per 1.5-2 moles of the compound.

Generally, for a compound containing n functions selected from e.g. ketone functions and amide functions, e.g. n amide functions, the molar ratio between $P_2S_5.2C_5H_5N$ and the compound may be from n/4 to n, or from n/4 to n/2, e.g. from n/4 to n/3.

An advantageous feature of $P_2S_5.2C_5H_5N$ as a thionating agent is its selectivity. Thus, for example carboxylic ester functions generally do not react with $P_2S_5.2C_5H_5N$, and therefore, the present invention also provides a method of selectively thionating e.g. an amide or keto function in a compound also comprising a carboxylic ester function.

The invention will be further described in the following, non-limiting examples.

Example 1

Crystalline $P_2S_5.2C_5H_5N$

Tetraphosphorus decasulfide ($P_4S_{10}$, 44.5 g, 0.1 mol) was added in portions to dry pyridine (560 mL) at 80° C. using stirring equipment. After a period of reflux (1 h) a clear yellow solution was obtained, which deposited light-yellow crystals when the solution was allowed to cool. After 2 h the crystals were collected, washed with dry acetonitrile and finally transferred to an exsiccator (containing a beaker with conc. sulfuric acid) to remove any excess of pyridine, yield 62.3 g (84%), mp: 167-169° C., IR $v_{max}$: 3088, 3040, 1608, 1451, 1197, 1044, 723, 668 cm$^{-1}$; cf. FIG. 1.

Pyridinium Dihydrogenmonothiophosphate

Figure 2A:
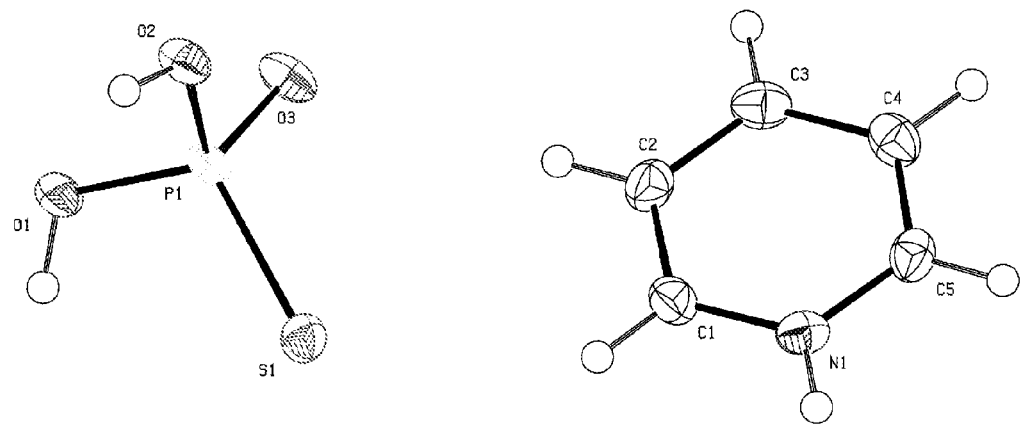
FIG. 2 shows (A) the molecular structure and (B) the crystal structure of pyridinium dihydrogenmonothiophosphate.
Figure 2B:
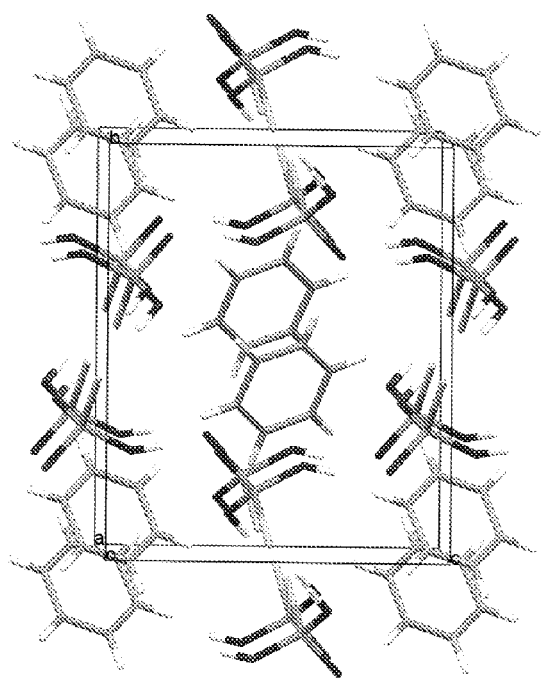

The crystalline $P_2S_5.2C_5H_5N$ (3.80 g, 10 mmol) was heated at reflux temperature in acetonitrile (35 mL) containing water (1.0 mL). The clear solution (obtained within 3 min) was concentrated and the product allowed to crystallize, 3.15 g, (79%). The crystals were suitable for X-ray crystallography, mp: 110-120° C., decomp., with evolution of $H_2S$; $^1H$ NMR (300 MHz, DMSO-$d_6$) δ 7.51 (m, 2H, 3-H), 7.95 (dd, 1H, 4-H), 8.63 (d, 2H, 2-H), 9.7 (br s, 3H); $^{13}C$ NMR (75.5 MHz, DMSO-$d_6$) δ 124.7 (d), 138.5 (d), 147.8 (d); cf. FIG. 2.

Pyridinium O,O-Diethyldithiophosphonate

The crystalline $P_2S_5.2C_5H_5N$ (1.0 g) was heated at reflux in ethanol (5 mL) for 5 min, the clear solution was evaporated to give an oil which soon solidified (100%).

IR $v_{max}$: 2976, 2891, 1630, 1600, 1526, 1479, 1383, 1020, 920, 748, 681 cm$^{-1}$ $^1H$ NMR (300 MHz, DMSO-$d_6$) δ 1.08 (t, J=7.1 Hz, 6H), 3.79 (m, 4H), 8.09 (m, 2H), 8.62 (m, 1H), 8.97 (m, 2H); $^{13}C$ NMR (75.5 MHz, DMSO-$d_6$) δ 16.1 (q, $^3J_{C-P}$=8.8 Hz), 59.8 (t, $^2J_{C-P}$=7.1 Hz), 127.2 (d), 142.5 (d), 146.0 (d).

Example 2

(S)-11-Thioxo-2,3,11,11a-tetrahydro-1H-benzo[e] pyrrolo[1,2-a][1,4]diazepine-5-(10H)-one (Table 1, Entry 17)

To a MeCN-solution (200 mL) of 2,3-dihydro-1H-benzo [e]pyrrolo[1,2-a][1,4]diazepine-5,11(10H,11aH)-dione (4.0 g, 20 mmol) crystalline $P_2S_5.2C_5H_5N$ (2.3 g, 6 mmol), was added and heated to 60° C. for 3 h during which time a yellow precipitate was formed. The reaction mixture was allowed to stand at room temperature overnight in order to precipitate fully. The product was vacuum-filtered and washed with a little cold MeCN to give the title compound (3.9 g, 85%) as a pale-yellow solid, mp 268-270° C.; $[\alpha]_D^{23}$+971° (c 0.16, MeOH); Ir $v_{max}$: 3170, 2979, 1616, 1602, 1477, 1374, 1271, 1141, 831, 813, 752 cm$^{-1}$;

$^1H$ NMR (300 MHz, DMSO-$d_6$) δ 1.89-1.94 (m, 1H), 1.99-2.16 (m, 2H), 2.84-2.94 (m, 1H), 3.40-3.50 (m, 1H), 3.53-3.60 (m, 1H), 4.27 (d, J=6.11 Hz, 1H), 7.22-7.27 (m, 1H), 7.30-7.37 (m, 1H), 7.55-7.60 (m, 1H), 7.80-7.85 (m, 1H), 12.46 (br s, 1H); $^{13}C$ NMR (75.5 MHz, DMSO-$d_6$) δ 22.7 (t), 29.0 (t), 46.8 (t), 59.8 (d), 121.8 (d), 125.7 (d), 127.8 (s), 130.2 (d), 132.2 (d), 136.5 (s), 164.2 (s), 201.9 (s).

Example 3

2,5-Piperazinedithione from Glycine
(Table 2, Entry 1)

Glycine (1.50 g, 20 mmol), crystalline $P_2S_5.2C_5H_5N$ (9.12 g, 28 mmol) and dimethylsulfone (8.0 g) were heated at 165-170° C. for 1 h whereupon the reaction mixture (after cooling) was treated with boiling water for 30 min. The brownish solid obtained was recrystallized from ethanol/DMF, 1.85 g (63%) mp 284° C.; $^1H$ NMR (300 MHz, DMSO-$d_6$) δ 4.19 (s), 10.7 (s); $^{13}C$ NMR (75.5 MHz, DMSO-$d_6$) δ 54.4 (q), 191.9 (s).

Example 4

2,5-Piperazinedithione from 2,5-Piperazinedione
(Table 2, Entry 2)

2,5-piperazinedione (2.28 g, 20 mmol) and crystalline $P_2S_5.2C_5H_5N$ (2.28 g, 8 mmol) were heated at reflux in acetonitrile (50 mL) for 2 h, when the mixture was concentrated and water was added. The solid formed was collected after a stirring period of 1 h, 2.63 g (90%). Melting point and NMR data are identical to data reported above for 2,5-piperazinedithione from glycine (Table 2, entry 1).

S,S'-1,4-Diacetyl-2,5-bis-acetylthiolo-1,4-dihydropyrazine, 35

The above 2,5-piperazinedithione (1.46 g, 10 mmol) was heated at reflux temperature in acetic anhydride (20 mL) for 2 h, whereupon the reaction mixture was concentrated and treated with diisopropyl ether, 2.06 g (93%), mp 190-192° C.; $^1H$ NMR (300 MHz, DMSO-$d_6$) δ 2.17 (s, 6H), 2.45 (s, 6H), 6.99 (s, 2H); $^{13}$C NMR (75.5 MHz, DMSO-$d_6$) δ 22.2 (q), 29.4 (q), 117.0 (s), 131.6 (d), 166.3 (s), 193.7 (s); Elemental analysis calcd for $C_{12}H_{14}N_2O_4S_2$, C, 45.75; H, 4.48; N, 8.88. Found C, 45.90; H, 4.32; N, 8.71.

Reductive Cleavage of the Tetrasulfide, 25

The 3,3'-diindolyl-2,2'-tetrasulfide 25, (3.58 g, 10 mmol was dissolved in THF, 50 mL and added to a mixture of NaBH$_4$ (1.50 g, 40 mmol) in THF (75 mL). Evolution of gases containing H$_2$S ensued and the reaction mixture was stirred for 3 h at 40-45° C. under a blanket of argon. This air-sensitive solution containing the dianion 26 was not stored but directly transformed by operations described below.

2,2'-Bis(methylthio)-1H,1'H-3,3'-biindole

Dimethyl sulfate (1.51 g, 12 mmol) dissolved in MeOH (15 mL) was added dropwise to a solution obtained by reductive cleavage of the tetrasulfide 25 (5 mmol) at 25° C. After a period (1 h) of stirring the solution was evaporated and treated with water. The crude solid was crystallized from MeOH-water to yield a yellow solid (0.45 g, 57%) mp 184-186° C.; $^1$H NMR (300 MHz, DMSO-$d_6$) δ 2.44 (s, 6H), 6.95-6.99 (m, 2H), 7.10-7.22 (m, 4H), 7.36-7.45 (m, 2H), 11.55 (s, 2H); $^{13}$C NMR (75.5 MHz, DMSO-$d_6$) δ 18.0 (q), 110.8 (s), 110.9 (d), 119.0 (d), 119.2 (d), 121.5 (d), 128.0 (s), 129.1 (s), 137.0 (s).

Synthesis of the Cyclodisulfide, 23

A solution obtained by reductive cleavage of the tetrasulfide 25 was, after addition of water (50 mL), stirred for 24 h in contact with air. The yellow solid formed was collected and crystallized from acetonitrile-DMF 4:1 yielding 2.20 g (77%) of a solid still containing DMF, which was removed by drying under reduced pressure, mp>227-228° C.
$^1$H NMR (300 MHz, DMSO-$d_6$) δ 7.04-7.08 (m, 1H), 7.28-7.31 (m, 2H), 7.33-7.51 (m, 1H), 12.16 (s, 1H); $^{13}$C NMR (75.5 MHz, DMSO-$d_6$) δ 136.3 (s), 127.0 (s), 124.9 (s), 124.6 (d), 120.3 (d), 120.2 (d), 119.3 (s), 112.2 (d).

Example 5

Cyclodisulfide 23 by Thionation of Oxindole at 160° C. (Table 3, Entry 13)

Oxindole (1.33 g, 10 mmol) and crystalline P$_2$S$_5$.2C$_5$H$_5$N (1.52 g, 4 mmol) were warmed with dimethylsulfone (4.0 g) and then heated at 160° C. for 5 min. The melt was allowed to cool and then heated with water. The solid formed was crystallized from acetonitrile-DMF 4:1 yielding 1.37 g (92%) mp>227-228° C. This material was identical with that obtained via reductive cleavage of the tetrasulfide 25.

3,3'-Bithio-oxindole, 27

The solution obtained from reductive cleavage of the tetrasulfide 25 was acidified with AcOH which resulted in quick formation of the title compound as a yellow precipitate, 2.52 g (85%). Which was recrystallized from acetonitrile, mp 180° C. decomp. This molecule is sensitive towards aerial oxidation.
$^1$H NMR (300 MHz, DMSO-$d_6$) δ 4.66 (s, 2H), 6.85-6.91 (m, 4H), 6.96-6.98 (m, 2H), 7.07-7.13 (m, 2H), 13.06 (s, 2H); $^{13}$C NMR (75.5 MHz, DMSO-$d_6$) δ 60.8 (d), 110.4 (d), 123.0 (d), 123.4 (d), 128.6 (d), 130.2 (s), 144.2 (s), 204.3 (s). Elemental analysis calcd for $C_{16}H_{12}N_2S_2$; C, 64.60; H, 4.081 N, 9.43. Found C, 64.26; H, 3.99; N, 9.31.

Example 6

Methyl 5-mercapto-4-(2-methoxy-2-oxoethyl)-2-methyl-1H-pyrrole-3-carboxylate, 34b The diester 33a (2.13 g, 10 mmol) and crystalline P$_2$S$_5$.2C$_5$H$_5$N (1.14 g, 4 mmol) were heated at reflux temperature in acetonitrile (50 mL) for 1 h. After concentration to 25 mL, water was added and the solid formed collected and crystallized from 2-propanol, 1.85 g (81%) mp. 185-187° C.; IR $v_{max}$: 3273, 2954, 1742, 1724, 1707, 1681, 1562, 1440, 1341, 1269, 1200, 1173, 1117, 1080, 1003, 782 cm$^{-1}$; $^1$H NMR (300 MHz, DMSO-$d_6$) δ 2.43 (s, 3H, CH$_3$), 3.17 (s, 1H, SH), 3.49 (s, 3H, OCH$_3$), 3.64 (s, 3H, OCH$_3$), 11.90 (s, 1H, NH); $^{13}$C NMR (75.5 MHz, DMSO-$d_6$) δ 13.4 (q), 30.6 (d), 50.4 (q), 51.4 (q), 111.2 (s), 117.1 (s), 126.9 (s), 139.9 (s), 164.4 (s), 171.1 (s) Elemental analysis calcd for $C_{10}H_{13}NO_4S$; C, 49.37; H, 5.38; N, 5.75. Found C, 49.25; H, 5.46; N, 5.61.

Example 7

3-(1H-Indol-3-yl)-3,3'-biindoline-2-thione (Table 3, Entry 9)

3-(1H-indol-3-yl)-3,3'-biindolin-2-one (728 mg, 2 mmol), crystalline P$_2$S$_5$.2C$_5$H$_5$N (228 mg, 0.6 mmol) and dimethylsulfone (3.05 g) were heated (165-170° C.) for 20 min. The melt was allowed to cool and then heated in water for 10 min. The solid formed was collected, 766 mg (94%), mp>260° C. $^1$H NMR (300 MHz, DMSO-$d_6$) δ 7.09-7.15 (m, 2H), 7.18-7.20 (m, 5H), 7.24-7.30 (m, 7H), 13.00 (s, 1H); $^{13}$C NMR (75.5 MHz, DMSO-$d_6$) δ 72.7 (s), 111.2 (d), 124.4 (d), 126.5 (d), 127.5 (d), 128.6 (s), 128.7 (s), 129.0 (d), 129.1 (d), 129.1 (d), 139.2 (s), 143.0 (s), 143.5 (s), 145.3 (s, 2C), 208.4 (s). Elemental analysis calcd for $C_{24}H_{17}N_3S$; C, 75.96; H, 4.51; N, 11.07. Found C, 76.10; H, 4.46; N, 11.00.

The outcome of a number of thionation reactions according to the invention, using crystalline P$_2$S$_5$.2C$_5$H$_5$N dissolved in hot acetonitrile, are listed in Table 1. In the exemplified reactions, the ratio of crystalline P$_2$S$_5$.2C$_5$H$_5$N to the compound to be thionated was 1.1:4. In some cases direct comparisons with LR have been made. For instance ε-caprolactam and P$_2$S$_5$.2C$_5$H$_5$N gave the corresponding thioamide within 5 min, but LR thionates even faster.

Actually, a suspension of LR in hot acetonitrile can be titrated by addition of ε-caprolactam. The advantages of the thionating agent of the invention over LR are primarily that the inventive thionating agent is easier to prepare, odourless (when sufficiently pure) and that the thionated products are very pure. In the Examples described herein, formation of nitriles from primary amides never was a problem. This type of side reaction can sometimes be problematic when the thionating agent LR is used[7,8]. Thionation of the exemplified ketones with P$_2$S$_5$.2C$_5$H$_5$N worked well (Table 2, entries 3 and 4). The keto derivatives 20a and 21a could be converted to 20b and 21b, respectively, when the thionating agent of the invention is used in hot pyridine or as a melt or even better—when heated together with dimethylsulfone (Table 1, entry 20 and Table 3, entry 3).

Whereas thionation of 3,3-dimethyloxindole (entry 7, Table 1) gave an excellent yield, the parent compound, oxindole (entry 6, Table 1) gave unacceptably low yields (~10%). Here, formation of complexes of low solubility seems to be the cause of the problems. Synthesis of 3,3-diindolylindoline-2-thione also failed but could be effected with dimethylsulfone as solvent (see Table 3). Thionation of 3-hydroxy-2-pyridone worked well without complications to give the interesting class of 3-hydroxy-2-(1H)-pyridinethione, which for several types of metal complexes (e.g. $Zn^{2+}$) have been reported to show some promise against diabetes mellitus.

In cases where more than one carbonyl group is present in the starting materials selectivity could be achieved. Thus the monothionated molecules (Table 1, entries 12, 16 and 17) could be obtained in good yields. Thionation of piperidine-2,6-dione gave the monothionated product in hot acetonitrile whereas with an excess of the thionating agent in hot pyridine the fully thionated product could be obtained.

TABLE 1

Thionation of amides with the inventive thionating agent in hot MeCN.

| Entry | Amide | Thioamide | Yield (%) | Mp ° C. |
|---|---|---|---|---|
| 1 | | | 98 | 114-116 |
| 2 | | | 98 | 115-116 |
| 3 | | | 99 | 105.5-106.5 |
| 4 | | | 85 | 117 |
| 5 | | | 88 | 147-148 |
| 6 | | | Low yield cf Table 3, entry 13 | 144-145 |
| 7 | | | 94 | 106-107 |
| 8 | | | 90 | 195 |
| 9 | | | 82 | 164-165 |

TABLE 1-continued

Thionation of amides with the inventive thionating agent in hot MeCN.

| Entry | Amide | Thioamide | Yield (%) | Mp ° C. |
|---|---|---|---|---|
| 10 | | | 96 | 99-100 |
| 11 | | | 92[a] | 110[a,] |
| 12 | | | 85 | 130-132 |
| 13 | | | 90 | 92-93 |
| 14 | | | 72 | 127-128 |
| 15 | | | 65 | 141 |
| 16 | | | 63 | 277-280 |
| 17 | | | 87 | 268-270 |
| 18 | | | 89 | 210-212 (decomp.) |

TABLE 1-continued

Thionation of amides with the inventive thionating agent in hot MeCN.

| Entry | Amide | Thioamide | Yield (%) | Mp °C. |
|---|---|---|---|---|
| 19 | 34a | 34b | 81 | 185-187 |
| 20 | 21a | 21b | 79 | 232 |

[a] isolated product contained two rotamers

Thionation of Gly-Gly as well as piperazine-2,5-dione both gave good yields of the expected dithionated product (Table 2, entries 1 and 2). To further characterise the rather insoluble product, it was acetylated in hot acetic anhydride, which yielded the tetraacetylated product 35 which readily gave nice NMR spectra.

TABLE 2

Thionation with the inventive thionating agent in hot pyridine

| Entry | Amide/ketone | Thioamide/thione | Yield (%) | Mp °C. |
|---|---|---|---|---|
| 1 | | | 78[a] | 285 |
| 2 | | | 90 | 285 |
| 3 | 18a | 19a | 82 | 120-121 |
| 4 | 18b | 19b | 74 | 200-202 |
| 5 | | | 96 | 297-298 |

TABLE 2-continued

Thionation with the inventive thionating agent in hot pyridine

| Entry | Amide/ketone | Thioamide/thione | Yield (%) | Mp ° C. |
|---|---|---|---|---|
| 6 | [3-hydroxyquinolin-2(1H)-one structure] | [3-hydroxyquinoline-2(1H)-thione structure] | 93 | >260 |
| 7 | [glutarimide structure] | [glutarodithione structure] | 90 | 105-106 |
| 8 | [quinoxaline-2,3-dione structure] | [quinoxaline-2-thione-3-thiol structure] | 83 | 298-300 |
| 9 | [2-phenylquinolin-4(1H)-one structure] | [2-phenylquinoline-4(1H)-thione structure] | 77 | 192-194 |

[a] obtained from DMF-H$_2$O

Thionations at quite high temperatures (165-175° C.) could be effected with e.g. P$_2$S$_5$.2C$_5$H$_5$N dissolved in dimethylsulfone (mp 107-109° C., by 238° C.). The results of some exemplifying reactions of the invention are listed in Table 3. In one case (Table 3, entry 6) the product was partially converted to the highly insoluble disulfide 22. Similar observations have been reported e.g. Stoyanov[9] and Hino et al[10]. The latter workers found that a number of 3-substituted indole-2-thiones readily could be oxidized to the corresponding disulfides. Formation of oxidative products could be avoided by running the reactions under argon.

Benzaldehyde has been thionated many times in the past[11-16] and the product has invariably been isolated as the trimer (29) of the unstable primary product 30, and the trimer 29, was indeed the product when benzaldehyde was reacted with the thionating agent of the invention in dimethylsulfone.

[structures 29 and 30]

Ester carbonyl groups are generally not attacked by P$_2$S$_5$.2C$_5$H$_5$N as can be exemplified by thionation (Table 3, entry 10) of the monoacetate of kojic acid (31) which selectively gave the thione 32 (Table 1, entry 17). Thionation of the diester 33a offered another example, namely the pyrrole-2-thiol derivative 34b

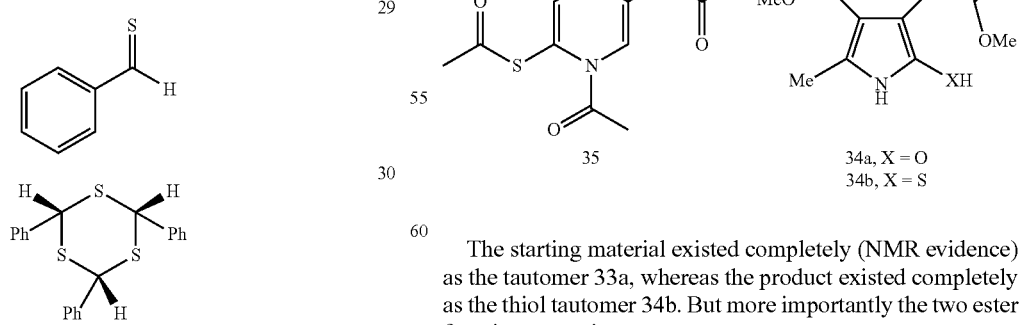

31, X = O
32, X = S

33a, X = O
33b, X = S

35

34a, X = O
34b, X = S

The starting material existed completely (NMR evidence) as the tautomer 33a, whereas the product existed completely as the thiol tautomer 34b. But more importantly the two ester functions were intact.

Due to low solubility and high melting point, 2,5-piperazinedithione (Table 3, entry 12) was difficult to characterize, therefore the readily soluble tetraacetate 35 was prepared.

TABLE 3

Thionation in dimethylsulfone with the inventive thionating agent at 165-175° C.

| Entry | Carbonyl compound | Thiocarbonyl compound | Yield (%) | Mp ° C. |
|---|---|---|---|---|
| 1 | acridin-9(10H)-one | acridine-9(10H)-thione | 90 | 274-276 |
| 2 | xanthen-9(9H)-one | xanthene-9(9H)-thione | 78 | 155 |
| 3 | 3-acetylindole (20a) | 3-(thioacetyl)indole (20b) | 53 | 144-145 |
| 4 | 4-amino-acridin-9(10H)-one | 4-amino-acridine-9(10H)-thione | 76 | 243-245 |
| 5 | indolo-quinolinone | indolo-quinolinethione | 95 | 335-337 |
| 6 | indolo-quinolinone isomer | indolo-quinolinethione isomer | 96 | >260 |
| 7 | benzaldehyde | 2,4,6-triphenyl-1,3,5-trithiane | 62 | 228 |
| 8 | thymine | dithiothymine | 78 | 280-282 |

TABLE 3-continued

Thionation in dimethylsulfone with the inventive thionating agent at 165-175° C.

| Entry | Carbonyl compound | Thiocarbonyl compound | Yield (%) | Mp ° C. |
|---|---|---|---|---|
| 9 | 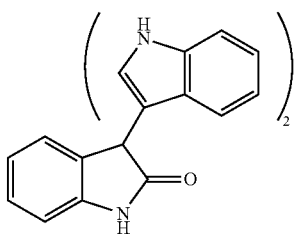 | 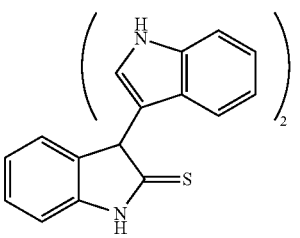 | 94 | >260 |
| 10 | 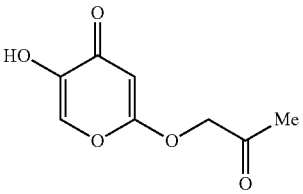 [SMILES: CC(=O)COc1cc(=O)c(O)co1] | 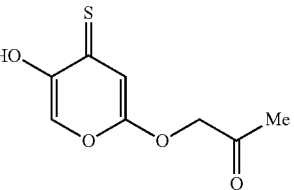 | 56 | 114-115 |
| 11 | 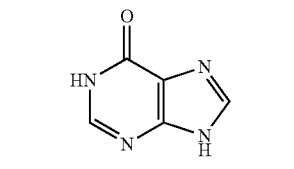 | 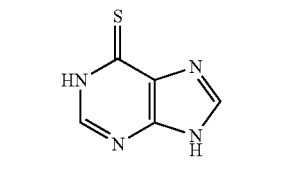 | 85 | >260 |
| 12 | 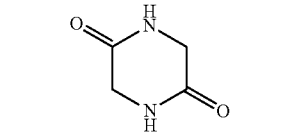 | 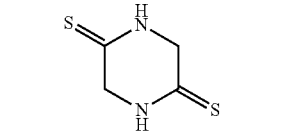 | 92[a] | >284 |
| 13 | 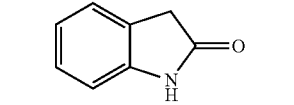 | 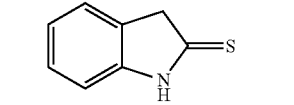 | 92[b] | 144-145 |

[a] starting from glycine
[b] experiment run under argon

In the light of the above general description and with further guidance from the illustrating Examples, the person of ordinary skill in the art will be well capable of practicing the invention within the full scope of the claims, using routine experimentation if necessary to select suitable reaction conditions, e.g. in view of the functional groups that may be present in the compound to be thionated. For example, the reaction may be performed under normal ambient atmosphere or under an inert atmosphere of e.g. argon or nitrogen. Other parameters that may be optimized or varied are e.g. the solvent medium, the reaction temperature and the reaction time and all such modifications and variations are contemplated to be within the scope of the present invention.

REFERENCES (1) Klingsberg, E.; Papa, D. J. Am. Chem. Soc. 1951, 73, 4988-4989.
(2) Meisel, M.; Grunze, H. Z. Anorg. Allg. Chemie, 1967, 360, 277-283.
(3) Fluck, E.; Binder, H. Z. Anorg. Allg. Chemie 1967, 354, 113-129.
(4) Brunel, E.; Monzur, J.; Retuert, J. J. Chem. Res (M) 1981, 3437-3445.
(5) Jesberger, M.; Davis, T. P.; Berner, L. Synthesis 2003, 1929-1958.
(6) a) Ozturk, T.; Erdal, E.; Olcay, M. Chem. Rev. 2007, 107, 5210-5278.
  b) Ozturk, T.; Erdal, E.; Olcay, M. Chem. Rev. 2010, 110, 3419-3478.
(7) Scheibye, S.; Shabana, R.; Lawesson, S. O.; Römming, C. Tetrahedron 1982, 38, 993-1001.
(8) Ley, S. V.; Leach, A. G.; Storer, R. I. J. Chem. Soc., Perkin Trans 1 2001, 358-361.
(9) Stoyanov, S.; Petkov, I.; Antonov, L.; T. Stoyanova; Karagiannidis, P.; Aslanidis, P. Can. J. Chem. 1990, 68, 1482-1489.
(10) Hino, T.; Suzuki, T.; Nakagawa, M. Chem. Pharm. Bull 1974, 22, 1053-1060.
(11) Baumann, E.; From, E. Ber. 1889, 22, 2600-2609.
(12) Stanfield, J. A.; Reynolds, L. B. J. Am. Chem. Soc. 1952, 74, 2878-2880.
(13) Böttcher, B.; Bauer, F. Liebigs Ann. Chem. 1951, 574, 218-226.

(14) Takikawa, Y.; Shimoda, K.; Makabe, T.; Takizawa, S. Chem. Lett. 1983, 1503-1506.

(15) Sekido, K.; Hirokawa, S. Acta. Cryst. C41 1985, 379-400.

(16) Bonini, B. F.; Mazzanti, G.; Zani, P.; Maccagani, G.; Foresti, E. J. Chem. Soc., Perkin Trans 1, 1988, 1499-1502.

The invention claimed is:

1. A thionating agent which is crystalline $P_2S_5.2C_5H_5N$ with a melting point of 167-169° C.

* * * * *